US00PP28336P3

(12) United States Plant Patent
Hunter

(10) Patent No.: US PP28,336 P3
(45) Date of Patent: Aug. 29, 2017

(54) PEAR TREE NAMED 'HW624'

(50) Latin Name: *Pyrus communis*
Varietal Denomination: HW624

(71) Applicant: Her Majesty the Queen in Right of Canada, as represented by the Minister of Agriculture & Agri-Food, Ottawa (CA)

(72) Inventor: David M. Hunter, St. Catharines (CA)

(73) Assignee: Agriculture and Agri-Food Canada, Ottawa (CA)

( * ) Notice: Subject to any disclaimer, the term of this patent is extended or adjusted under 35 U.S.C. 154(b) by 283 days.

(21) Appl. No.: 14/545,134

(22) Filed: Mar. 31, 2015

(65) Prior Publication Data

US 2016/0295760 P1 Oct. 6, 2016

(51) Int. Cl.
*A01H 5/08* (2006.01)

(52) U.S. Cl.
USPC ..... Plt./176

(58) Field of Classification Search
USPC ..... Plt./176
CPC ..... A01H 5/0881
See application file for complete search history.

(56) References Cited

PUBLICATIONS http://www.virtualorchard.net/idfta/cft/1999/april/hunter/08%20Hunter.pdf; Feb. 20-24, 1999; 6 pages.*
Canadian Plant Breeder's Rights Registration Certificate No. 4402 granted Sep. 6, 2012 for 'HW624' *Pyrus communis* variety.

* cited by examiner

*Primary Examiner* — Kent L Bell
(74) *Attorney, Agent, or Firm* — Brunet & Co.; Hans Koenig

(57) ABSTRACT

The invention is a new and distinct pear tree variety denominated 'HW624'. The new pear tree is characterized by producing heavy crops of medium-to large-sized fruit, picked about 2 weeks after 'Bartlett'. Fruits are green when harvested, turning yellow as fruits ripen, and there is a medium red blush where exposed to the sun. There were no natural fire blight infections on the seedling tree, and results from controlled inoculations indicate a high level of resistance to fire blight. The tree is also highly resistant to pear psylla.

2 Drawing Sheets

Latin name of the genus and species of the plant claimed: *Pyrus communis*.
Variety denomination: 'HW624'.

BACKGROUND OF THE INVENTION

The new and distinct pear tree described and claimed herein originated from a controlled cross between 'Harrow Sweet' and 'NY10353' made in 1988 in Harrow, Ontario. Pedigree of 'HW624' is shown in FIG. 1.

'HW624' was selected as a hybrid seedling ('H8806-1') in 1995 and propagated by budding on pear seedling rootstocks. Trees were planted in an evaluation orchard in 1999 in Jordan Station, Ontario. This selection was advanced and tested in regional trials beginning in 2000.

'HW624' is harvested two weeks after 'Bartlett', whereas 'Harrow Sweet' is harvested three and a half weeks after 'Bartlett' and 'NY10353' is harvested one week before 'Bartlett'. 'HW624' has medium to large size fruit, whereas 'Harrow Sweet' also has medium to large size fruit and 'NY10353' has small, plump spindle shaped fruit. 'HW624' fruit is yellow with a Red Blush at maturity, whereas 'Harrow Sweet' fruit is yellow at maturity. 'HW624' has a high level of resistance to fire blight and psylla, whereas 'Harrow Sweet' has good resistance to fire blight and 'NY10353' has good resistance to psylla and fire blight.

SUMMARY OF THE INVENTION

On the new pear tree 'HW624', the profile of the sides of the fruit of 'HW624' is straight whereas they are concave on the reference varieties 'Bosc' (R1), 'Harrow Sweet' (R2), 'AC Harrow Crisp' (R3) and 'Bartlett' (R4). The ground colour of the skin of 'HW624' is yellow whereas it is yellow green on 'Bosc', 'Harrow Street' and 'Bartlett'. 'HW624' has a medium to large area of over colour of the skin whereas there is none on 'Bosc', small to medium area on 'Harrow Street' and very small on 'Bartlett'. The over colour of 'HW624' is dark red whereas it is orange red on 'Harrow Street', 'AC Harrow Crisp' and 'Bartlett'. 'HW624' has no russetting around the eye basin, on the cheeks or around the stalk attachment of the fruit whereas 'Bosc' has a large to very large area. The fruit stalk of 'HW624' is thin whereas it is medium thickness on 'Harrow Street' and 'AC Harrow Crisp' and thick on 'Bartlett'. 'HW624' has weak curvature of the fruit stalk whereas the curvature is medium to strong on 'Bosc', medium on 'AC Harrow Crisp' and absent on 'Bartlett'. The attitude of the sepals on the fruit of 'HW624' is spreading whereas it is erect on 'Bosc' and 'Harrow Street' and converging on 'AC Harrow Crisp' and 'Bartlett'. 'HW624' is resistant to moderately resistant to fireblight (*Erwinia amylovora*) whereas 'Bosc' is moderately susceptible and 'Bartlett' is susceptible. 'HW624' is resistant to moderately resistant to pear psylla (*Cacopsylla pyricola* Foerst) whereas the reference varieties are susceptible.

The following are major distinguishing characteristics. 'HW624' is a mid-late season pear cultivar for the fresh market. 'HW624' produces heavy crops of medium-to large-sized fruit, picked about 2 weeks after 'Bartlett'. Fruits are green when harvested, turning yellow as fruits ripen, and there is a medium red blush where exposed to the sun. The tree has consistently produced heavy crops, with no evidence of biennial bearing. There were no natural fire blight infections on the seedling tree, and results from controlled inoculations indicate a high level of resistance to fire blight. The tree is also highly resistant to pear psylla (*Cacopsylla pyricola* Foerst). In years when orchard populations of psylla have been high, trees of 'HW624' have had no noticeable presence of this insect pest. 'HW624' is not graft-compatible with quince rootstocks. The characteristics most useful in distinguishing 'HW624' are fruit characteristics and resistance to fire blight and resistance to pear psylla.

BRIEF DESCRIPTION OF THE DRAWING

The accompanying photographic illustration illustrates in full color 'HW624'. The colors are as nearly true as reasonably possible in color representation of this type. Colors in the photographs may differ from the color values cited in the detailed botanical description below, which accurately describes the colors of the new pear tree.

DETAILED BOTANICAL DESCRIPTION OF THE INVENTION

Figure 1:
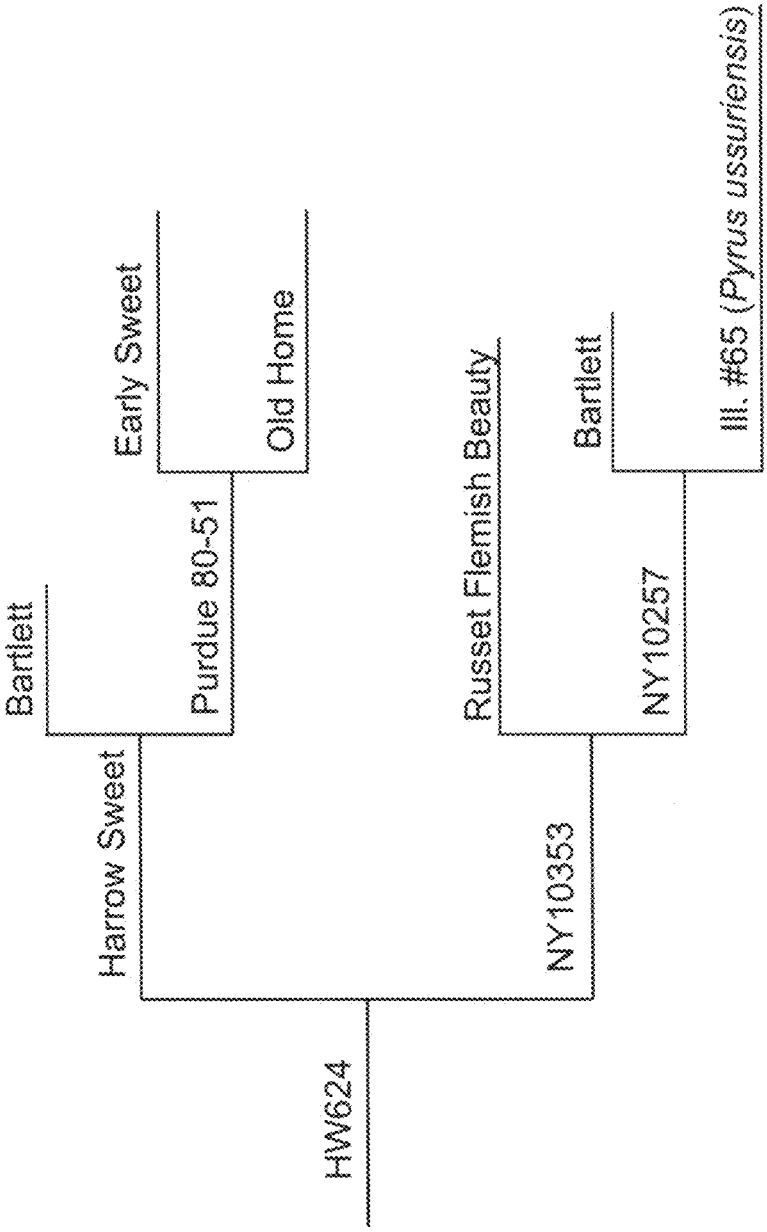
FIG. 1 shows pedigree of 'HW624'.
Figure 2:
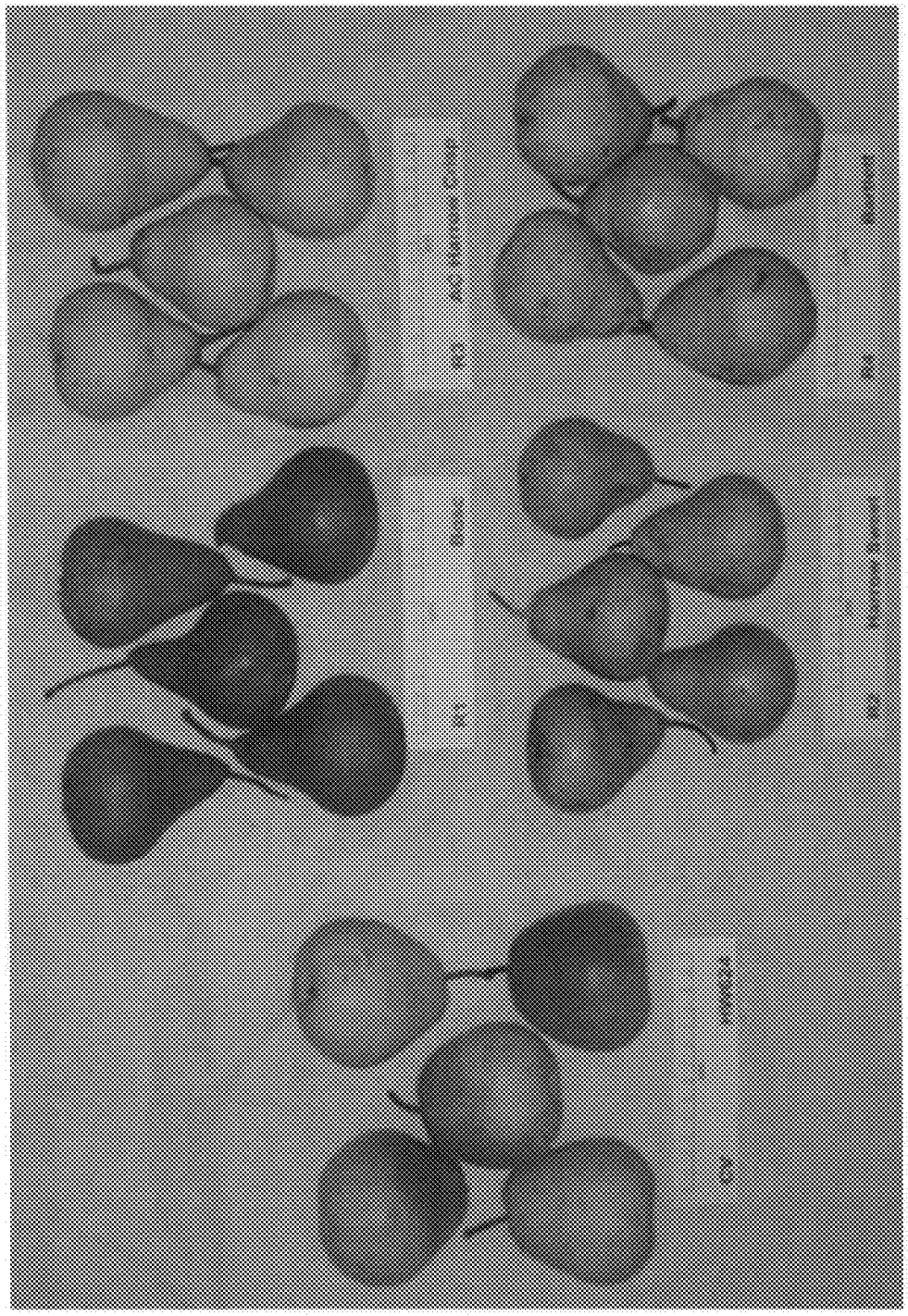
FIG. 2 shows five examples of the fruit of 'HW624' compared to the fruit of 'Bosc' (R1), 'Harrow Sweet' (R2), 'AC Harrow Crisp' (R3) and 'Bartlett' (R4).

The 'HW624' variety is uniform and stable. Asexual propagation maintains uniformity and stability. No off-types, variants or mutations have been found to date. Virus-tested 'HW624' is maintained in North Saanich, British Columbia.

The R.H.S. Colour Chart of The Royal Horticultural Society 1966 version has been used for colour identification of fruit and shoot. The description is based on observation of four trees grafted on seedling rootstock originally established during the 1999 growing season. Comparisons were made with 'Bosc' (R1), 'Harrow Sweet' (R2), 'AC Harrow Crisp' (R3) and 'Bartlett' (R4). Four trees of each variety grafted on 'Bartlett' open pollinated seedling rootstock were spaced about 3 metres apart with about 4.5 metres between rows and were observed during the 2009-2010 growing seasons in Jordan Station, Ontario. Fire blight evaluations and observations were conducted in 1988-2000 in Harrow, Ontario. 'HW624' was observed to be able to survive winter conditions (−29° C.) in Southwestern Ontario, Canada, while still having a full crop the following season. The observed chilling range for 'HW624' is 800-1000 hours, measured during the dormant period temperature below 45° F.

| | 'HW624' | R1 | R2 | R3 | R4 |
|---|---|---|---|---|---|
| Tree: | | | | | |
| Vigor | medium to strong | very strong | medium to strong | strong | medium |
| Branching | strong | medium to strong | strong | medium to strong | medium |
| Habit | spreading to drooping | spreading | spreading | spreading | spreading |

-continued

| | 'HW624' | R1 | R2 | R3 | R4 |
|---|---|---|---|---|---|
| Mature height (ft.) | near 12 | | | | |
| Mature spread (ft.) | near 10 | | | | |
| Trunk diameter 30 cm above ground (mm) | near 130 | | | | |
| Trunk colour | 197B | | | | |
| Branch length (cm) | near 50 | | | | |
| Branch diameter (mm) | near 8 | | | | |
| Branch crotch angle | near 35° | | | | |
| Branch texture | smooth | | | | |
| Branch colour | 177B | | | | |

| | 'HW624' | R1 | R2 |
|---|---|---|---|
| Shoot—One-year-old: | | | |
| Growth | wavy | wavy | wavy |
| Length of internode (cm) | | | |
| Mean | 3.42 | 4.28 | 3.02 |
| Std. deviation | 0.37 | 0.67 | 0.48 |
| Length of shoot (cm) | near 15 | | |
| Diameter of shoot (mm) | near 4 | | |
| Texture | smooth | | |
| Predominant colour on sunny side | brown purple (178A) | brown purple | orange brown |
| Number of lenticels | many (near 15 per $cm^2$) | many | medium to many |
| Shape of lenticels | oblong | | |
| Height of lenticels (mm) | near 2.5 | | |
| Diameter of lenticels (mm) | near 1 | | |
| Colour of lenticels | 156A | | |
| Shape of apex of vegetative bud | acute | acute | acute |
| Position of vegetative | slightly held | slightly held | slightly held |
| bud in relation to shoot | out | out to markedly held out | out |
| Length of vegetative bud (mm) | near 15 | | |
| Diameter of vegetative bud (mm) | near 2 | | |
| Colour of vegetative bud | 143B | | |
| Size of bud support | medium | small to medium | small to medium |
| Shoot—Young: | | | |
| Anthocyanin colouration of growing tip (during rapid growth) | very strong (180A) | strong to very strong | medium |
| Intensity of pubescence (upper third) | weak to medium | weak to medium | weak to medium |

| | R3 | R4 |
|---|---|---|
| Shoot—One-year-old: | | |
| Growth | straight to wavy | straight to wavy |
| Length of internode (cm) | | |
| Mean | 3.26 | 3.55 |
| Std. deviation | 0.58 | 0.46 |
| Length of shoot (cm) | | |
| Diameter of shoot (mm) | | |
| Texture | | |
| Predominant colour on sunny side | medium brown | orange brown |

-continued

| | | |
|---|---|---|
| Number of lenticels | medium to many | medium to many |
| Shape of lenticels | | |
| Height of lenticels (mm) | | |
| Diameter of lenticels (mm) | | |
| Colour of lenticels | | |
| Shape of apex of vegetative bud | acute | acute |
| Position of vegetative bud in relation to shoot | slightly held out | adpressed |
| Length of vegetative bud (mm) | | |
| Diameter of vegetative bud (mm) | | |
| Colour of vegetative bud | | |
| Size of bud support | medium | small to medium |
| Shoot—Young: | | |
| Anthocyanin colouration of growing tip (during rapid growth) | medium to strong | medium |
| Intensity of pubescence (upper third) | weak to medium | medium |

| | 'HW624' | R1 | R2 |
|---|---|---|---|
| Leaf—Blade: | | | |
| Attitude in relation to shoot | outwards | downwards | outwards |
| Length (cm) | | | |
| Mean | 6.5 | 7.1 | 7.1 |
| Std. deviation | 1.0 | 1.3 | 1.2 |
| Width (cm) | | | |
| Mean | 4.3 | 4.3 | 3.8 |
| Std. deviation | 0.7 | 1.0 | 0.8 |
| Length/Width ratio | small to medium | medium | medium to large |
| Leaf shape | elliptic | | |
| Shape of base | right-angled | obtuse | right-angled |
| Shape of apex (excluding pointed tip) | obtuse | right-angled | right-angled |
| Length of pointed tip | short | short | short |
| Incisions of margins (upper half) | bluntly serrate | crenate | bluntly serrate |
| Depth of incisions of margin | shallow | shallow | shallow |
| Curvature of longitudinal axis | very weak | weak to medium | weak |
| Leaf texture—top | smooth | | |
| Leaf texture—bottom | smooth | | |
| Leaf colour—top | 137B | | |
| Leaf colour—bottom | 147B | | |
| Leaf—Petiole: | | | |
| Length (cm) | | | |
| Mean | 2.7 | 2.2 | 2.4 |
| Std. deviation | 0.6 | 1.0 | 0.7 |
| Diameter (mm) | near 1.2 | | |
| Colour | 144C | | |
| Presence of stipules | present | Absent or weakly present | present |
| Distance of stipules from basal attachment of petiole | medium to long | medium | short to medium |

| | R3 | R4 |
|---|---|---|
| Leaf—Blade: | | |
| Attitude in relation to shoot | outwards | outwards |
| Length (cm) | | |
| Mean | 6.3 | 6.5 |
| Std. deviation | 0.8 | 0.7 |
| Width (cm) | | |
| Mean | 3.8 | 3.9 |
| Std. deviation | 0.7 | 0.6 |
| Length/Width ratio | medium | medium |
| Leaf shape | | |
| Shape of base | right-angled to obtuse | right-angled to obtuse |
| Shape of apex (excluding pointed tip) | right-angled | right-angled to obtuse |
| Length of pointed tip | short to very short | short |
| Incisions of margins (upper half) | bluntly serrate | bluntly serrate |
| Depth of incisions of margin | shallow | shallow |
| Curvature of longitudinal axis | weak | very weak |
| Leaf texture—top | | |
| Leaf texture—bottom | | |
| Leaf colour—top | | |
| Leaf colour—bottom | | |
| Leaf—Petiole: | | |
| Length (cm) | | |
| Mean | 2.1 | 2.0 |
| Std. deviation | 0.7 | 0.8 |
| Diameter (mm) | | |
| Colour | | |
| Presence of stipules | present | present |
| Distance of stipules from basal attachment of petiole | short to medium | short |

| | 'HW624' | R1 | R2 |
|---|---|---|---|
| Flower: | | | |
| Time of beginning of flowering | Early (May) | medium to late | early to medium |
| Time of full bloom | May | | |
| Location of flower bud on shoot | mainly on spurs | mainly on spurs | mainly on spurs |
| Length of flower bud (cm) | | | |
| Mean | 5.4 | 5.9 | 5.5 |
| Std. deviation | 0.7 | 0.5 | 0.6 |
| Shape of flower bud | obtuse | | |
| Diameter of flower bud (mm) | near 5 | | |
| Colour of flower bud | 49D | | |
| Flower diameter (mm) | near 2 | | |
| Flower depth (mm) | near 1 | | |
| Flower fragrance | nutty/almond | | |
| Number of flowers per cluster | 7 | | |
| Sepal length (cm) | | | |
| Mean | 5.9 | 8.3 | 6.7 |
| Std. deviation | 0.6 | 0.7 | 0.7 |
| Attitude of sepals in relation to corolla | recurved | recurved | recurved |
| Sepal number | 5 | | |
| Sepal shape | obtuse | | |
| Sepal width | (mm) | near 2 | |
| Sepal apex and margin | reddish and pointed apex and margin | | |
| Sepal texture—top | smooth | | |
| Sepal texture—bottom | smooth | | |
| Sepal colour—top | 22A | | |
| Sepal colour—bottom | 35B | | |
| Arrangement of petals | not touching to touching | not touching | touching to overlapping |
| Petal number | 5 | | |
| Petal shape | irregular | | |
| Petal apex and margin | irregular | | |
| Petal texture—top | smooth | | |
| Petal texture—bottom | smooth | | |
| Petal colour—top | NN155C | | |

-continued

| | | | |
|---|---|---|---|
| Petal colour—bottom | NN155C | | |
| Position of stigma in relation to stamens | same level | same level | above |
| Size of petal (length/width (mm)) | small to medium (10/12) | medium | medium |
| Shape of petal (excluding the claw) | circular to broad ovate | ovate | circular |
| Shape of base of petal (excluding the claw) | cuneate to rounded | cuneate | rounded |
| Length of claw of petal | short | medium | medium |
| Anther number | 12 | | |
| Anther length (mm) | near 3 | | |
| Pollen colour | N200A | | |
| Stigma length (mm) | near 0.1 | | |
| Stigma colour | 155B | | |
| Ovary colour | 192D | | |

| | R3 | R4 |
|---|---|---|
| Flower: | | |
| Time of beginning of flowering | medium to late | medium |
| Time of full bloom | | |
| Location of flower bud on shoot | mainly on spurs | mainly on spurs |
| Length of flower bud (cm) | | |
| Mean | 6.3 | 4.1 |
| Std. deviation | 0.4 | 0.3 |
| Shape of flower bud | | |
| Diameter of flower bud (mm) | | |
| Colour of flower bud | | |
| Flower diameter (mm) | | |
| Flower depth (mm) | | |
| Flower fragrance | | |
| Number of flowers per cluster | | |
| Sepal length (cm) | | |
| Mean | 7.9 | 7.0 |
| Std. deviation | 1.1 | 1.2 |
| Attitude of sepals in relation to corolla | recurved | spreading to recurved |
| Sepal number | | |
| Sepal shape | | |
| Sepal width | | |
| Sepal apex and margin | | |
| Sepal texture—top | | |
| Sepal texture—bottom | | |
| Sepal colour—top | | |
| Sepal colour—bottom | | |
| Arrangement of petals | touching | touching to overlapping |
| Petal number | | |
| Petal shape | | |
| Petal apex and margin | | |
| Petal texture—top | | |
| Petal texture—bottom | | |
| Petal colour—top | | |
| Petal colour—bottom | | |
| Position of stigma in relation to stamens | same level | same level |
| Size of petal (length/width (mm)) | small to medium | medium |
| Shape of petal (excluding the claw) | circular | circular |
| Shape of base of petal (excluding the claw) | rounded | Rounded |
| Length of claw of petal | very short | short |
| Anther number | | |
| Anther length (mm) | | |
| Pollen colour | | |
| Stigma length (mm) | | |
| Stigma colour | | |
| Ovary colour | | |

| | 'HW624' | R1 | R2 |
|---|---|---|---|
| Fruit: | | | |
| Length (cm) | | | |
| Mean | 8.7 | 10.2 | 9.1 |
| Std. deviation | 1.0 | 0.9 | 0.9 |
| Maximum diameter (cm) | | | |
| Mean | 6.9 | 7.0 | 6.6 |
| Std. deviation | 0.6 | 0.5 | 0.6 |
| Length/Diameter ratio | small to medium | medium to large | medium |
| Position of maximum diameter | slightly towards calyx | slightly towards calyx to clearly towards calyx | slightly towards calyx |
| Size | large | large | medium |
| Shape | slightly asymmetric | | |
| Symmetry (in longitudinal section) | slightly asymmetric | slightly asymmetric to strongly asymmetric | slightly asymmetric |
| Profile of sides | straight | concave | concave |
| Weight (g)—mean | 159.45 | | |
| Ground colour of skin | Yellow (11B) | yellow green | yellow green |
| Relative area of over colour | medium to large | absent or very small | small to medium |
| Hue of over colour | dark red (42B) | | orange red |
| Relative area of russet around eye basin | absent or very small | large to very large | absent or very small |
| Relative area of russet on cheeks | absent or very small | large to very large | absent or very small |
| Relative area of russet around stalk attachment | absent or very small | large to very large | absent or very small |
| Length of stalk (mm) | | | |
| Mean | 3.2 | 5.0 | 3.4 |
| Std. deviation | 0.7 | 0.7 | 0.6 |
| Thickness of stalk | thin (near 4 mm) | thin to medium | medium |
| Curvature of stalk | weak | medium to strong | weak to medium |
| Attitude of stalk in relation to axis of fruit | oblique | oblique | oblique |
| Depth of stalk cavity | medium to deep (near 5 mm) | absent or very shallow | shallow |
| Diameter of stalk cavity | near 15 mm | | |
| Attitude of sepals (at harvest) | spreading | erect | erect |
| Eye basin (at harvest) | present | present | present |
| Depth of eye basin (at harvest) | medium to deep (near 10 mm) | shallow | shallow |
| Width of eye basin (at harvest) | medium (near 35 mm) | narrow to medium | medium to broad |
| Relief of area around eye (at harvest) | slightly ribbed | slightly ribbed | slightly ribbed |
| Texture of flesh | very fine | very fine | very very fine |
| Firmness of flesh | medium to firm | medium | soft to medium |
| Juiciness of flesh | medium to juicy | juicy | juicy to very juicy |
| Flesh brix | 11.8 to 13.5 | | |
| Flesh colour | 158C | | |
| Fruit locule number per fruit | 5 | | |
| Fruit locule length (mm) | near 10 | | |
| Fruit locule width (mm) | near 6 | | |

-continued

| | | | |
|---|---|---|---|
| Seed shape | ovate | ovate | elliptic |
| Seed length (mm) | near 8 | | |
| Seed width (mm) | near 4 | | |
| Number of seeds per fruit | 3 to 5 | | |
| Number of seeds per locule | 1 | | |
| Seed colour | 165B-C | | |
| Time of maturity for consumption | Late (September) | very late | very late |
| Observed harvest dates of fruit | Sep. 18, 2013<br>Sep. 23, 2014<br>Sep. 19, 2015<br>Sep. 14, 2016 | | |
| Fruit production (lbs per tree per year) | 120 | | |

| | R3 | R4 |
|---|---|---|
| Fruit: | | |
| Length (cm) | | |
| Mean | 9.1 | 9.0 |
| Std. deviation | 0.8 | 0.9 |
| Maximum diameter (cm) | | |
| Mean | 6.8 | 6.8 |
| Std. deviation | 0.6 | 0.6 |
| Length/Diameter ratio | medium | small to medium |
| Position of maximum diameter | slightly towards calyx | in middle |
| Size | large | medium to large |
| Shape | | |
| Symmetry (in longitudinal section) | slightly asymmetric | symmetric to slightly asymmetric |
| Profile of sides | concave | concave |
| Weight (g)—mean | | |
| Ground colour of skin | yellow | yellow green |
| Relative area of over colour | medium | between very small and small |
| Hue of over colour | orange red | orange red |
| Relative area of russet around eye basin | absent or very small | absent or very small |
| Relative area of russet on cheeks | absent or very small | absent or very small |
| Relative area of russet around stalk attachment | small | very small to small |
| Length of stalk (mm) | | |
| Mean | 3.7 | 2.8 |
| Std. deviation | 0.9 | 0.6 |
| Thickness of stalk | medium | thick |
| Curvature of stalk | medium | absent or very weak |
| Attitude of stalk in relation to axis of fruit | straight to oblique | straight to oblique |
| Depth of stalk cavity | medium | medium |

-continued

| | | |
|---|---|---|
| Diameter of stalk cavity | | |
| Attitude of sepals (at harvest) | converging | converging |
| Eye basin (at harvest) | present | present |
| Depth of eye basin (at harvest) | shallow to medium | deep |
| Width of eye basin (at harvest) | medium | narrow |
| Relief of area around eye (at harvest) | smooth | embossed |
| Texture of flesh | very very fine | very very fine |
| Firmness of flesh | medium | medium to firm |
| Juiciness of flesh | medium to juicy | juicy |
| Flesh brix | | |
| Flesh colour | | |
| Fruit locule number per fruit | | |
| Fruit locule length (mm) | | |
| Fruit locule width (mm) | | |
| Seed shape | elliptic | ovate |
| Seed length (mm) | | |
| Seed width (mm) | | |
| Number of seeds per fruit | | |
| Number of seeds per locule | | |
| Seed colour | | |
| Time of maturity for consumption | medium | medium to late |
| Observed harvest dates of fruit | | |
| Fruit production (lbs per tree per year) | | |

| | 'HW624' | R1 | R2 |
|---|---|---|---|
| Disease/Pest Reactions: | | | |
| Fire blight (*Elwininia amylovora*) | resistant to moderately resistant | moderately susceptible | resistant to moderately resistant |
| Pear psylla (*Cacopsylla pyricola*) | resistant to moderately resistant | susceptible | susceptible |

| | R3 | R4 |
|---|---|---|
| Disease/Pest Reactions: | | |
| Fire blight (*Elwininia amylovora*) | resistant to moderately resistant | susceptible |
| Pear psylla (*Cacopsylla pyricola*) | susceptible | susceptible |

The 'HW624' variety has not been observed under all possible environmental conditions to date. Accordingly, it is possible that the phenotypic expression may vary somewhat with changes in light intensity and duration, cultural practices, and other environmental conditions.

What is claimed:

1. A new and distinct variety of pear tree substantially as herein illustrated and described.

* * * * *